US009078939B2

(12) United States Patent
Dornau et al.

(10) Patent No.: US 9,078,939 B2
(45) Date of Patent: Jul. 14, 2015

(54) DISINFECTANT SYSTEM

(75) Inventors: Gregor Dornau, Fort Lauderdale, FL (US); Peter Dornau, Fort Lauderdale, FL (US)

(73) Assignee: Star-Brite Distributing, Inc., Fort Lauderdale, FL (US)

( * ) Notice: Subject to any disclaimer, the term of this patent is extended or adjusted under 35 U.S.C. 154(b) by 790 days.

(21) Appl. No.: 13/356,069

(22) Filed: Jan. 23, 2012

(65) Prior Publication Data

US 2013/0186974 A1 Jul. 25, 2013

(51) Int. Cl.
| | | |
|---|---|---|
| *A61L 2/18* | (2006.01) | |
| *A61L 2/20* | (2006.01) | |
| *A61L 2/23* | (2006.01) | |
| *A61L 9/05* | (2006.01) | |
| *A61L 9/12* | (2006.01) | |

(52) U.S. Cl.
CPC ... *A61L 2/18* (2013.01); *A61L 2/20* (2013.01); *A61L 2/23* (2013.01); *A61L 9/05* (2013.01); *A61L 9/12* (2013.01); *A61L 2202/11* (2013.01)

(58) Field of Classification Search
CPC ............... A61L 2/18; A61L 2/20; A61L 2/23; A61L 9/05; A61L 9/12
See application file for complete search history.

(56) References Cited

U.S. PATENT DOCUMENTS

| | | | |
|---|---|---|---|
| 2,022,262 A | | 11/1935 | White |
| 2,071,091 A | | 2/1937 | Taylor |
| 2,071,094 A | | 2/1937 | Vincent |
| 2,482,891 A | | 9/1949 | Aston |
| 3,690,320 A | * | 9/1972 | Riely ............... 604/333 |
| 4,185,754 A | * | 1/1980 | Julius ............... 221/63 |
| 4,200,610 A | * | 4/1980 | Swaine et al. ........ 422/239 |
| 4,366,804 A | * | 1/1983 | Abe ............... 126/263.02 |
| 4,585,482 A | | 4/1986 | Tice et al. |
| 4,588,561 A | * | 5/1986 | Aswell et al. ........ 422/238 |
| 4,748,904 A | | 6/1988 | Razeto et al. |
| 5,023,012 A | | 6/1991 | Buchan et al. |
| 5,091,107 A | * | 2/1992 | Hutchings ........... 252/187.21 |
| 5,407,656 A | | 4/1995 | Roodzar |
| 6,046,243 A | | 4/2000 | Wellinghoff et al. |
| 6,063,425 A | | 5/2000 | Kross et al. |
| 6,726,386 B1 | * | 4/2004 | Gruenbacher et al. ...... 401/7 |
| 6,764,661 B1 | | 7/2004 | Girard |
| 7,021,848 B1 | * | 4/2006 | Gruenbacher et al. ...... 401/1 |
| 7,108,440 B1 | * | 9/2006 | Gruenbacher et al. ...... 401/132 |
| 2004/0022676 A1 | * | 2/2004 | Hamilton et al. ........ 422/37 |
| 2009/0142235 A1 | * | 6/2009 | Rico et al. ............ 422/129 |

FOREIGN PATENT DOCUMENTS

| | | |
|---|---|---|
| CA | 959238 | 12/1974 |
| WO | 9924356 | 5/1999 |

* cited by examiner

*Primary Examiner* — Regina M Yoo
(74) *Attorney, Agent, or Firm* — Christopher & Weisberg, P.A.

(57) ABSTRACT

A disinfectant system including a pouch enclosing a first reagent, the first reagent releasing a disinfecting vapor when exposed to moisture. A moisture transfer element is included engageable with the pouch.

18 Claims, 5 Drawing Sheets

DISINFECTANT SYSTEM

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for generating and dispersing gaseous disinfectant.

BACKGROUND OF THE INVENTION

The most common system and method for delivering disinfectants to surfaces, for example, tile, wood, granite, plastic, and glass is through the use of spray bottles containing a disinfectant solution, typically comprising an alcohol. The user operates the spray bottle by aiming the bottle's nozzle in the direction of the surface to be treated and applying pressure to a plunger, which causes the release of the disinfectant in a small particle fluid form. However, because fluids from spray bottles are dispersed as a bolus, and rely on the precise aim of the user, portions of surfaces may remain untreated and therefore potentially infected with pathogens or materials causing noxious odors. Moreover, such disinfectant solutions are ineffective at removing airborne pathogens.

To address airborne odors, bacteria, and viruses, aerosols have been utilized to disinfect and deodorize the ambient air in an enclosed area, such as in a home, car, or cabin on a boat or plane. The dispersal of the fluid from canister or bottle may be achieved by repeated plunging of a lever that sprays a predetermined amount of fluid, or alternatively, the canister may continuously spray fluid so long as the plunger is depressed. However, similar to surface disinfectants, aerosol disinfectant delivery systems can only deliver disinfectant for a limited time and to a limited area. While gases from aerosols may substantially fill an area by entropic forces, because disinfectant gases from aerosols are not constantly released they are not effective at disinfecting substantially entire spaces rapidly.

Another method and system of deodorizing room may include providing plug-in or wall mounted units defining a reservoir that releases deodorizing particles. Drawbacks of such systems include, limited portability, as some units require electricity to operate; limited operability, as some units are motion activated; a predetermined rate of disinfectant release, as the disinfectant is released at a constant rate, and as a result, are of limited effectiveness, as none of the units on the market provide for both rapid release and slow release of gaseous disinfectant particles to sanitize a particular space.

It is therefore desirable to provide for a portable disinfectant system that disinfects a particular space either rapidly or slowly and that does not require electricity or constant activation by the user.

SUMMARY OF THE INVENTION

The present invention advantageously provides a disinfectant system including a pouch enclosing a first reagent, the first reagent releasing a disinfecting vapor when exposed to moisture. A moisture transfer element is included engageable with the pouch.

In another embodiment, the disinfectant system includes a pouch enclosing a first moisture activated reagent, the first reagent releasing a disinfecting vapor when exposed to moisture. A moisture transfer element defining a slit is included, the pouch being removeably insertable within the slit. A container defining a plurality of apertures is included, the pouch and the moisture transfer element being received within the container.

In yet another embodiment, the disinfectant system includes a pouch enclosing a first moisture activated reagent releasing a disinfecting vapor when exposed to moisture. A sponge defining a slit substantially though a midpoint of the sponge is included, the pouch being removeably insertable within the slit, the sponge transferring moisture to the pouch when the pouch is inserted within the slit. A container including a pivotally coupled hatch is included, the hatch defining a plurality of apertures, the pouch and the moisture transfer element being received within the container.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
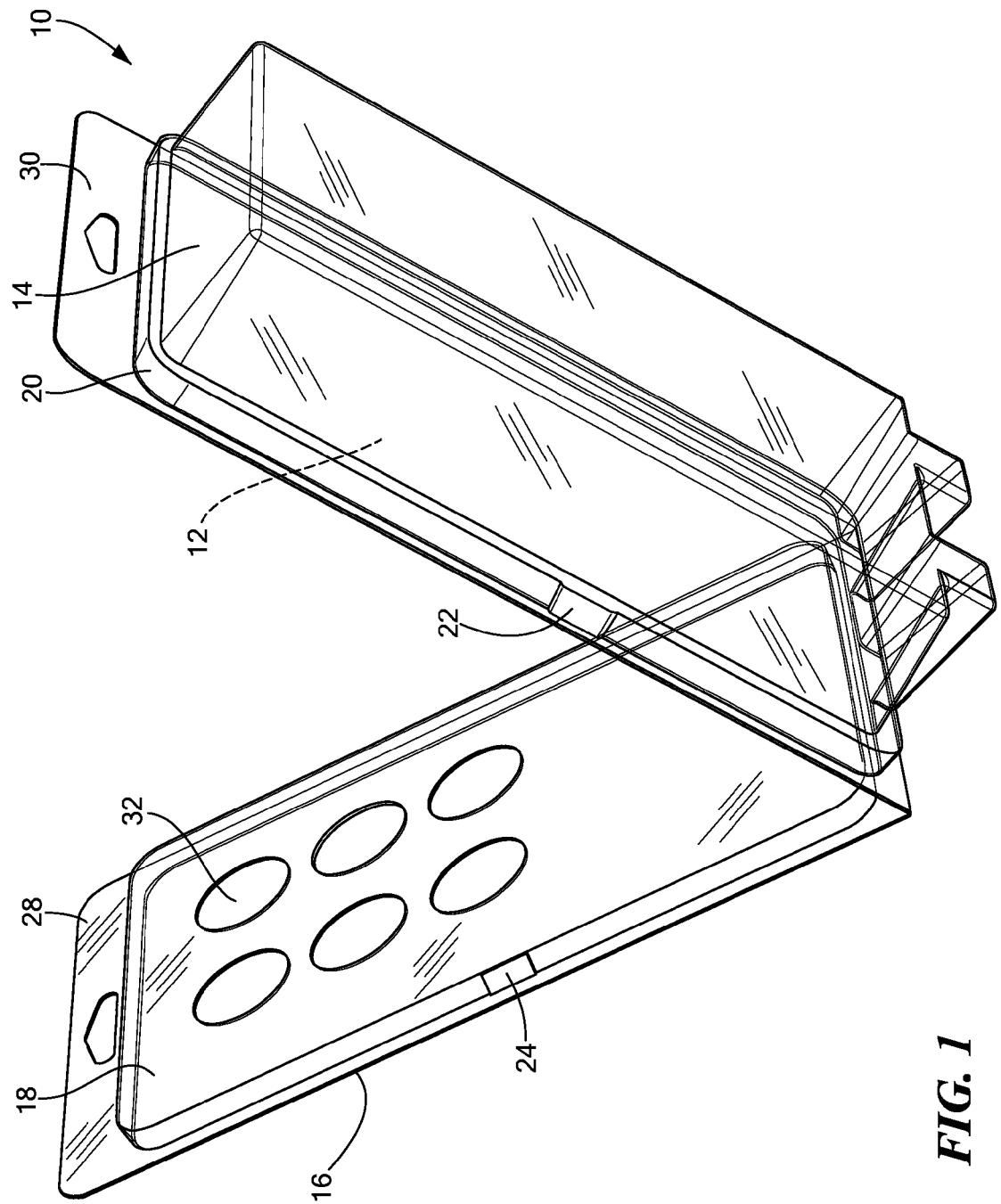
FIG. 1 is a perspective view of an exemplary container of the disinfectant system constructed in accordance with the principles of the present invention.

Referring now to the drawings in which like reference designators refer to like elements, there is shown in FIG. 1 an exemplary container of the disinfectant system constructed in accordance with the principles of the present invention and designated generally "10." The container 10 may be composed any non-reactive materials, and in particular, plastics, metals or any material sufficiently light such that it is portable. In an exemplary embodiment, the container 10 may be composed of a flexible plastic, for example, polyethylene terephthalate, and may be a clam-shell shape to provide for easy access to the interior of the container 10. For example, the container 10 may define an opening 12 on a face of the container 10. In particular, the container 10 may be a body portion 14 that may include a plurality of walls or other structures operable to enclose an object such as a disinfectant device within. The walls may be substantially impermeable to gasses to liquids, or alternatively may be semi-permeable to gasses.

Covering the opening 12 may be a hatch 16 which is sized to at least substantially fit within the opening 12 to substantially close the opening 12. The hatch 16 may be pivotally coupled to one of walls of the container 10, for example, with a hinge or other mechanism operable to facilitate the movement of the hatch 16 from a closed position in which the hatch covers the opening 12 to an open position in which the interior of the container is accessible. Alternatively, the hatch 16 may be removable from the body portion 14 and may cover a portion of the opening 12. In the particular configuration shown in FIG. 1, the hatch 16 includes an elevated portion 18 sized to fit within a complimentary recess 20 defined by the body portion 14. For example, the elevated portion 18 may define dimensions commensurate with the dimensions of the recess 20 such that when the hatch 16 is in a closed positioned the elevated portion 18 fits snuggly within the recess 20.

The body portion 14 may further define a tab 22 protruding from a portion of the recess 20, the tab 22 being sized to fit within a corresponding groove 24 defined by the elevated portion 18. For example, as the hatch 16 is moved into the opening 16 from an open position to a closed position, the tab 22 and the groove 24 engage each other such that the hatch 16 is removeably secured to the recess 20. To facilitate the opening and closing of the hatch 16, a first lip 28 and a second lip 30 may surround the perimeters of the elevated portion 18 and recess 20 respectively to provide a surface to grip to separate the hatch 16 from the recess 20.

The body portion 14 and/or hatch 16 may further define a plurality of apertures 32 disposed, for example, on the surface of the hatch 16. The size and number of apertures 32 is variable depending on the desired rate of air flux from released from the container 10. In particular, the larger the size and number of apertures 32, the faster the disinfectant release from the container 10. In an exemplary embodiment, six apertures 32 are defined by the hatch, the apertures 32 defining a diameter of approximately one inch.

Figure 2:
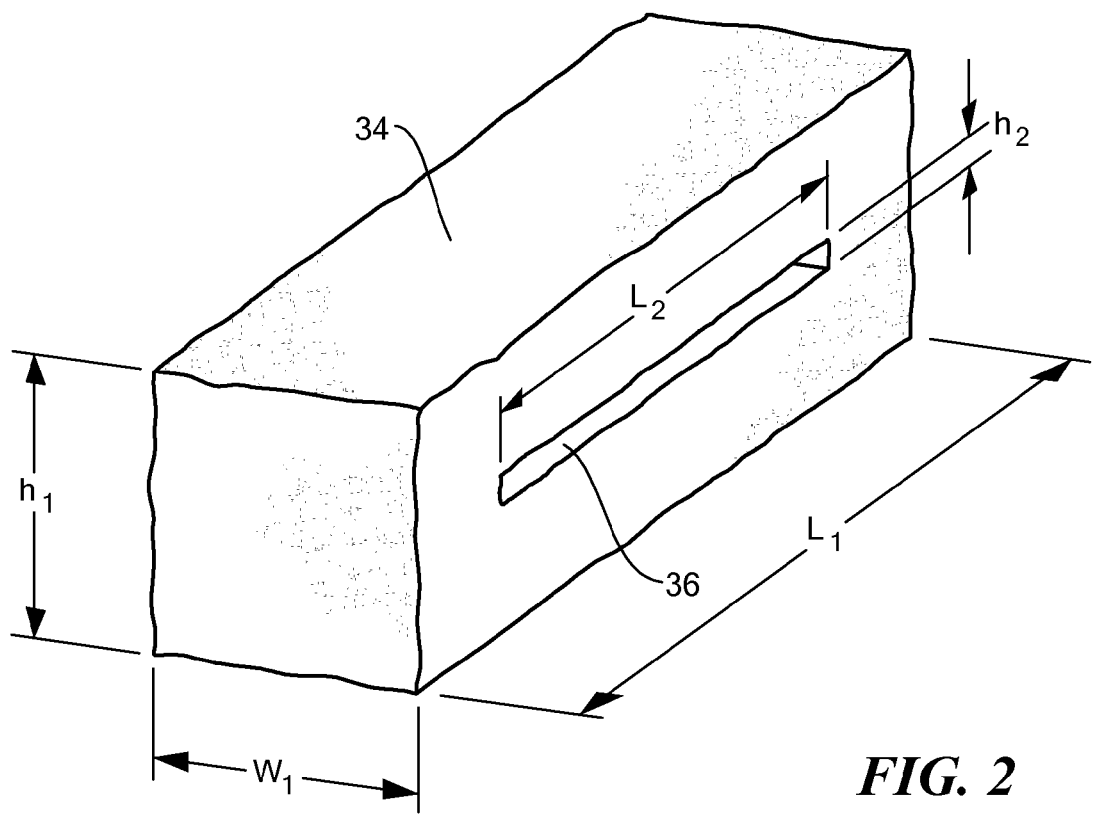
FIG. 2 is a perspective view of a moisture transfer element constructed in accordance with the principles of the present invention.

Now referring to FIG. 2, receivable within the container 10 may be a moisture absorbing and releasing element 34. The moisture transfer element 34 may be for example, a sponge, or other material, or combination of materials, which may absorb and retain water and/or water vapor for a period of time and then release it to a proximate structure. In the configuration shown in FIG. 2, the moisture transfer element 34 is a sponge approximately an inch in height ("$h_1$") and width ("$w_1$"), and approximately three inches in length ("$l_1$"). The size of the moisture transfer element 34 may be variable depending on the desired rate of release of disinfecting vapor from the container 10, but in an exemplary configuration, the size of the moisture transfer element 34 is no larger than a substantial portion of the interior of the container 10.

The moisture transfer element 34 may further define a slit 36 defined on at least a portion of the moisture transfer element 34. For example, as shown in FIG. 2, the slit is defined along a length of the sponge 34 and extends through approximately the midpoint of the sponge. The slit 36 may extend entirely though the width of the sponge such that the slit 26 is accessible from more than one side of the sponge 34, or alternatively may extend through a portion of the width of the sponge 34. The slit 36 may be any dimension and in an exemplary embodiment is approximately 0.1 millimeter in height ($h_2$) and approximately two inches in length ($l_2$) with $l_2$ being less than $l_1$.

Figure 3:
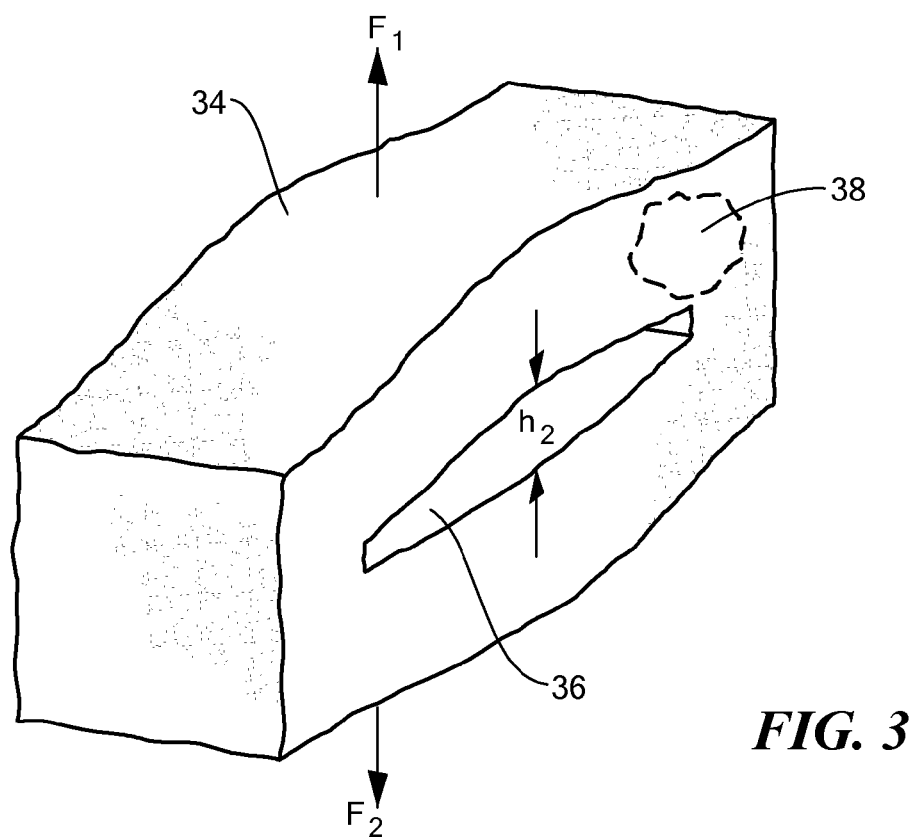
FIG. 3 is a perspective of the moisture transfer element in FIG. 2 showing the slit expanded.

Referring now to FIG. 3, because $l_2$ is less than $l_1$, pulling forces $F_1$ and $F_2$ applied to the sponge 34 causes the slit 36 to widen such that $h_2$ is increased. The increase in height of the slit 36 allows for insertion on thin object within the slit 36. When the pulling forces $F_1$ and $F_2$ are ceased the sponge 36 returns to original biased position with the object disposed within the slit 36 and a force applied to the object by the sponge 34. The sponge 34 may further define one or more compartments 38 sized to retain a fluid, for example, water. The compartments 38 may be composed of a flexible material and any may rupture upon the applicant of a force, for example, a twisting force. For example, the compartment 38 may be pre-filled with volume of water. When the sponge 34 is twisted or torqued, the compartment 38 ruptures, releasing the water to the sponge, which results in the sponge being moistened.

Figure 4:
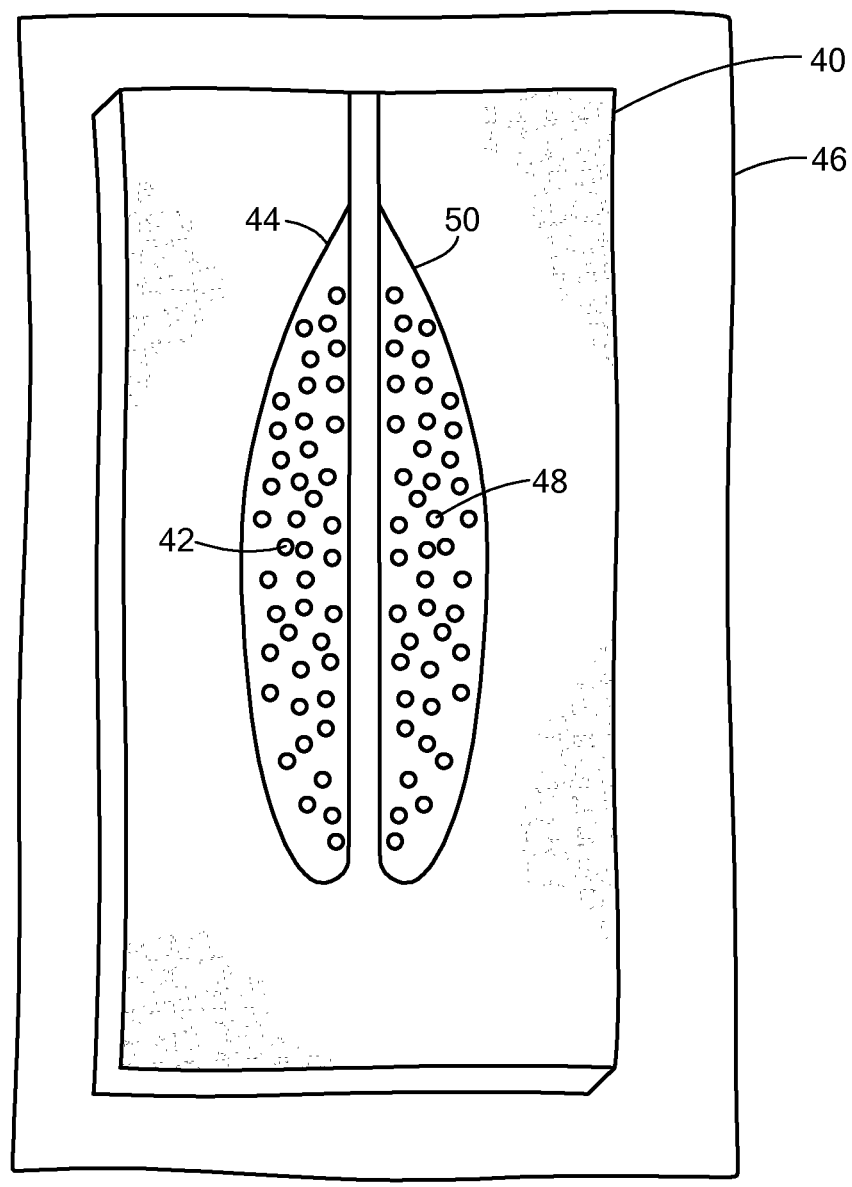
FIG. 4 is a top cross-sectional view of an exemplary pouch constructed in accordance with the principles of the present invention.

Now referring to FIG. 4, also retained within the container 10 may a pouch 40 at least partially filled with a disinfectant reagent 42 and sized to fit within the container 10. The pouch 40 may include one or more chambers 44 for retaining the disinfectant reagent 42. In an exemplary embodiment, the pouch 40 and/or the one or more chambers 44 may be semi-permeable to water vapor and impermeable to the reagent 42. For example, the pouch 42 may define a plurality of slots or pores to increase the flow rate of water vapor into the chamber 44 as disclosed and described in U.S. Publication No. 2009/0142235, the entirety of which is incorporated herein by reference. The pouch 40 may further be disposed in a protective enclosure 46 that is substantially impermeable to water to prevent premature activation of the reagent 42. The protective enclosure 46 may be composed of MYLAR or other similar materials. The pouch 40 may be removed from the protective enclosure 46 by, for example, tearing a portion the protective enclose 46 and sliding out the pouch 40.

In an exemplary embodiment, the reagent 42 is in a powder form spread about the chamber 44 to provide for a larger surface area to react with water. The reagent 42 may be any compound, chemical, or polymer that reacts with a substance, for example, water, to produce a disinfecting vapor. For example, in an exemplary embodiment, the reagent 42 may contain, in part, chlorite, which may release chlorine dioxide gas when exposed to moisture and/or water vapor. The rate at which chlorine dioxide is released from the pouch 40 depends on the amount of moisture and/or water present surrounding and penetrating the pouch 40. In particular, the more water and/or water vapor present around the pouch 10, the greater the increase in the rate of chlorine dioxide production. Thus, the rate at which disinfectant is released from the pouch 40 may be varied depending on the amount of water present in proximity to the pouch 40. A second reagent 48 may also disposed with the chamber 44 or a second chamber 50. The second reagent 48 may a fragrant releasing reagent such that in addition to the pouch releasing a disinfecting vapor, it may also release a fragrance.

The pouch 40 may further define a width such that the pouch 40 is removeably inserted within the slit 36 of the sponge 34. In particular, the pouch 40 may be sufficiently narrow and sufficiently thin such that it may be slid within the slit 36. For example, depending on the height $h^2$ the slit 36 the pouch 40 may be pushed within the slit 36 such that it engages and is friction fit with the sponge 34. Additionally, the position of the pouch 40 in relation to the sponge 34 may be varied by sliding the pouch 40 within the slit 36 by applying a pulling force to the sponge 34 to expand $h_2$, as discussed above, such that the pouch 40 is moveable within the slit 36 to a desired position.

Figure 5:
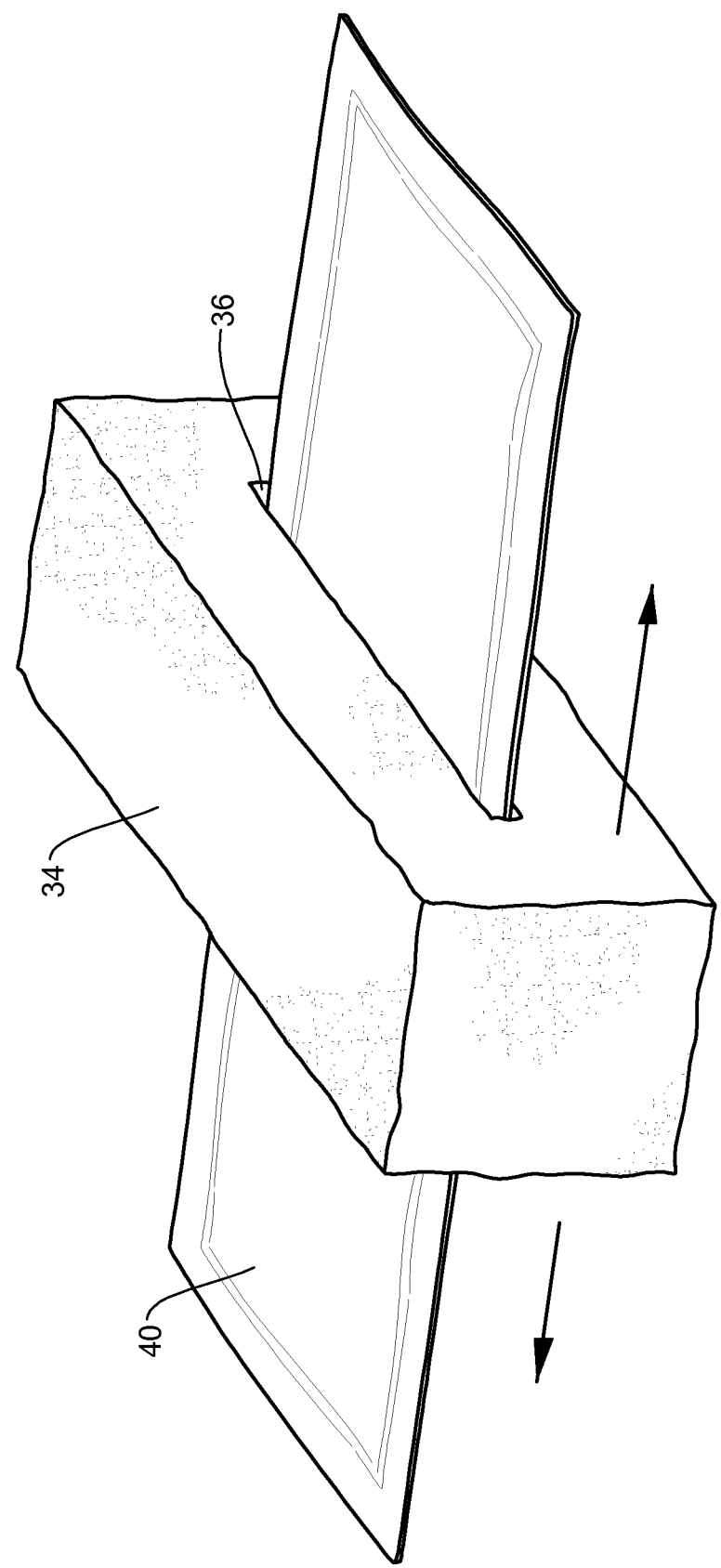
FIG. 5 is a perspective view showing the pouch in FIG. 4 inserted within the moisture releasing element of FIG. 2.

For example, as shown in FIG. 5, it may be desirable to orient the sponge 34 in relation to the pouch 40 (indicated by the directional arrows) such that the sponge 34 is positioned in substantially the center of the pouch 40, along the length of the pouch, to allow for maximum water diffusion from the sponge 34, in both directions, onto the pouch 40. In an exemplary configuration, a horizontal axis defined by the sponge 34 coplanar with the slit 36 is substantially coplanar with a horizontal axis defined by the pouch 40. In another configuration, the sponge 34 may be positioned at a distal end of the pouch 40 such that the pouch 40 extends from the sponge 34 as a cantilever. In such a configuration, when the sponge 34 is moistened, the water diffuses longitudinally away from the sponge 34 onto the pouch 40. As such, portions of the pouch 40 most distal the sponge 34 become moistened slower that portions proximal the sponge 34. Accordingly, the rate at which disinfectant vapor is released from the pouch 40 may be varied depending on the position of the pouch 40 relative to the sponge 34. The more centered the wet or damp sponge 34 is with respect to the pouch 40 the faster the release of disinfectant vapors.

Figure 6:
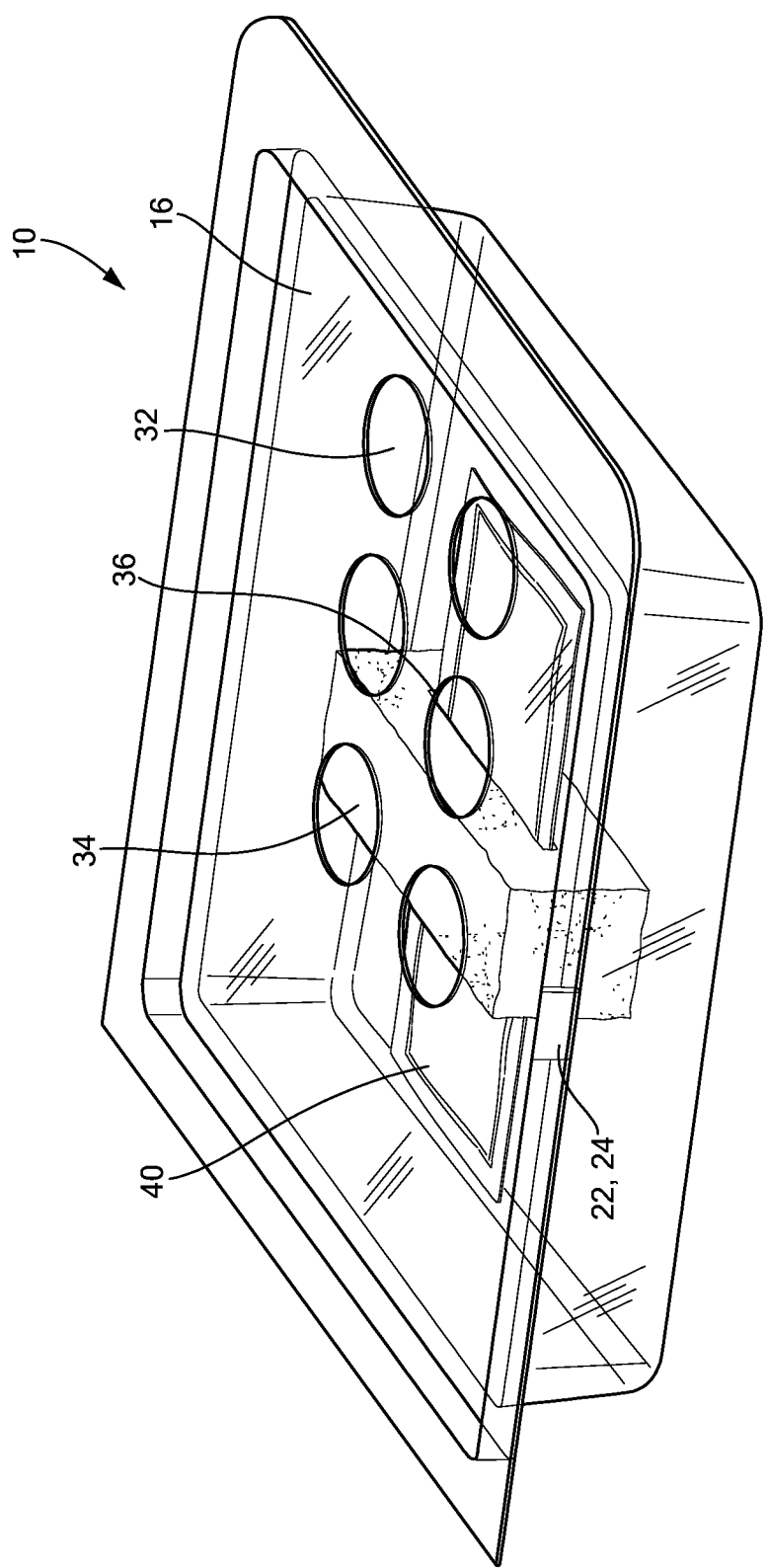
FIG. 6 is a perspective view showing the pouch and moisture transfer element shown in FIG. 5 disposed within the container of FIG. 1.

Now referring to FIG. 6, the sponge 34 and pouch 40 may be coupled together and received within the container 10. Alternatively, the sponge 34 may be placed in proximity to the pouch 40 when disposed within the container 10. The sponge 34 may be dampened before insertion into the container 10 or after, and additional water may be added to the container 10 when the sponge 34 and pouch 40 are disposed within the container. The hatch 16 may be closed and disinfecting vapor may be generated and released from the pouch 40 out through the apertures 32. As discussed above, the rate at which disinfecting vapor is generated may depend on the volume of water vapor and/or water within the container 10 and within the sponge 34. In particular, a volume of water may be poured into the container 10 where it may be absorbed by the sponge 34 and the pouch 40 to accelerate the release of disinfecting particles. Further, the container, along with the sponge 34 and the pouch 40, may be portable and movable while the pouch is releasing disinfecting particles.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A disinfectant system, comprising:
a pouch enclosing a first reagent, the first reagent releasing a disinfecting vapor when exposed to moisture;
a moisture transfer element releaseably engageable with the pouch, the pouch being removeably insertable within a portion of the moisture transfer element; and
the moisture transfer element defines a slit, and wherein the pouch is removeably insertable within the slit.

2. The disinfectant system of claim 1, wherein the moisture transfer element is a sponge.

3. The disinfectant system of claim 1, wherein the pouch includes a second reagent different than the first reagent.

4. The disinfectant system of claim 3, wherein the first reagent and the second reagent are isolated from each other within the pouch.

5. The disinfectant system of claim 1, further comprising a container, and wherein the pouch and the moisture transfer element are received and enclosed within the container.

6. The disinfectant system of claim 5, wherein the container defines a plurality of apertures.

7. The disinfectant system of claim 6, wherein the container defines an opening, and wherein the container includes a hatch sized to releaseably close the opening.

8. The disinfectant system of claim 7, wherein the hatch defines the plurality of apertures.

9. The disinfectant system of claim 7, wherein the hatch is pivotally coupled to the container.

10. A disinfectant system, comprising:
a pouch enclosing a first moisture activated reagent, the first moisture activated reagent releasing a disinfecting vapor when exposed to moisture;
a moisture transfer element defining a slit, the pouch being removeably insertable within the slit; and
a container defining a plurality of apertures, the pouch and the moisture transfer element being received within the container.

11. The disinfectant system of claim 10, wherein the moisture transfer element is a sponge.

12. The disinfectant system of claim 10, wherein the container defines an opening, and wherein the container includes a hatch sized to releaseably close the opening.

13. The disinfectant system of claim 12, wherein the hatch defines a plurality of apertures.

14. The disinfectant system of claim 13, wherein the hatch is pivotally coupled to the container.

15. The disinfectant system of claim 10, wherein the pouch includes a second moisture activated reagent different than the first reagent.

16. The disinfectant system of claim 15, wherein the first moisture activated reagent and the second moisture activated reagent are isolated from each other within the pouch.

17. The disinfectant system of claim 16, further comprising a moisture absorbing membrane within the pouch, and wherein the moisture absorbing membrane is in fluid communication with the first moisture activated reagent and the second moisture activated reagent.

18. A disinfectant system, comprising:
a pouch enclosing a first moisture activated reagent releasing a disinfecting vapor when exposed to moisture;
a sponge defining a slit substantially though a midpoint of the sponge, the pouch being removeably insertable within the slit, the sponge transferring moisture to the pouch when the pouch is inserted within the slit; and
a container including a pivotally coupled hatch, the hatch defining a plurality of apertures, the pouch and the sponge being received within the container.

\* \* \* \* \*